United States Patent [19]

Nugent et al.

[11] Patent Number: 4,967,763

[45] Date of Patent: Nov. 6, 1990

[54] PLATELET STABLE BLOOD COLLECTION ASSEMBLY

[75] Inventors: Edward Nugent, North Caldwell, N.J.; Robert J. Losada, Astoria, N.Y.; Hugh T. Conway, Verona, N.J.; David B. Montgomery; Joel L. Williams, both of Cary, N.C.

[73] Assignee: Becton, Dickinson and Company, Franklin Lakes, N.J.

[21] Appl. No.: 322,474

[22] Filed: Mar. 13, 1989

[51] Int. Cl.$^5$ .............................................. A61B 5/14
[52] U.S. Cl. .................................................... 128/763
[58] Field of Search ............... 128/760, 763, 765, 770; 604/317, 411, 414

[56] References Cited

U.S. PATENT DOCUMENTS

| | | | |
|---|---|---|---|
| 4,024,857 | 5/1977 | Blecher et al. | 128/763 |
| 4,397,318 | 8/1983 | Burns | 128/763 |
| 4,646,753 | 3/1987 | Nugent | 128/763 |
| 4,653,512 | 3/1987 | Losada | 128/763 |
| 4,690,153 | 9/1987 | Losada et al. | 128/763 |

Primary Examiner—Max Hindenburg
Attorney, Agent, or Firm—Richard E. Brown

[57] ABSTRACT

A blood collection assembly includes a plasma-treated blood collection container and a blood collector which optionally may also be plasma-treated. The collector has a body portion providing a blood passageway between the container and a scoop shaped portion which contacts a puncture wound. A vent in the collector allows air displacement from the container when blood enters. The inside wall of the container has longitudinal ribs molded thereon and an altered surface chemistry characterized by an enhanced oxygen content. The invention includes a method to increase blood flow across the interior surface of a plastic blood collection container comprising plasma treatment of the surface.

15 Claims, 4 Drawing Sheets

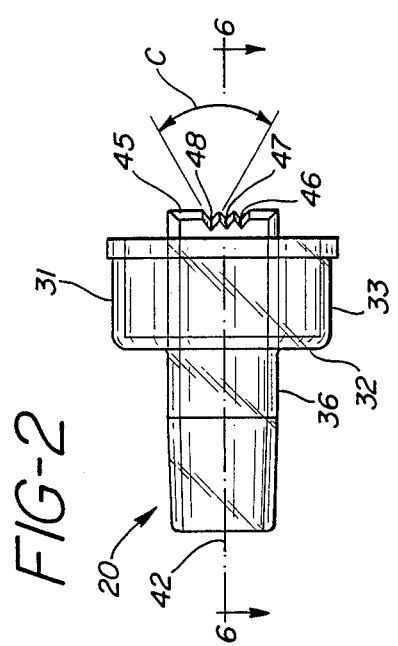
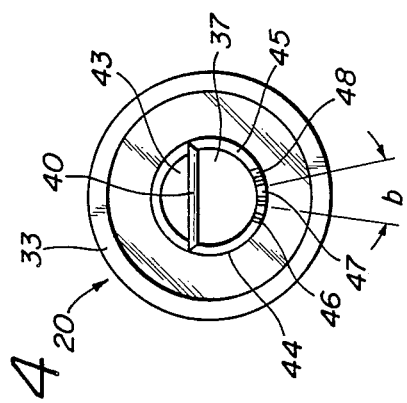
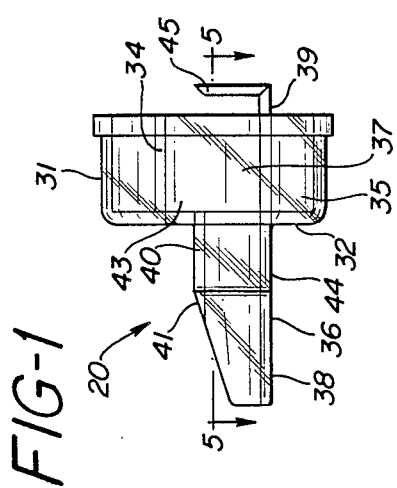
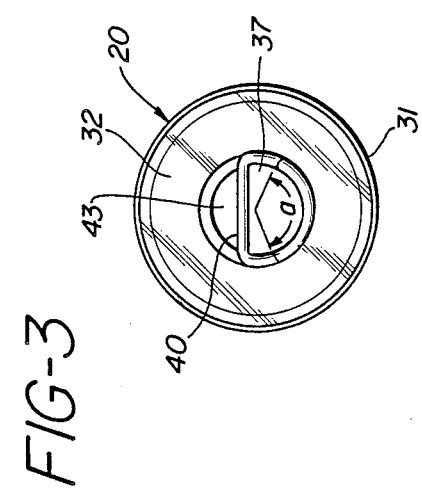

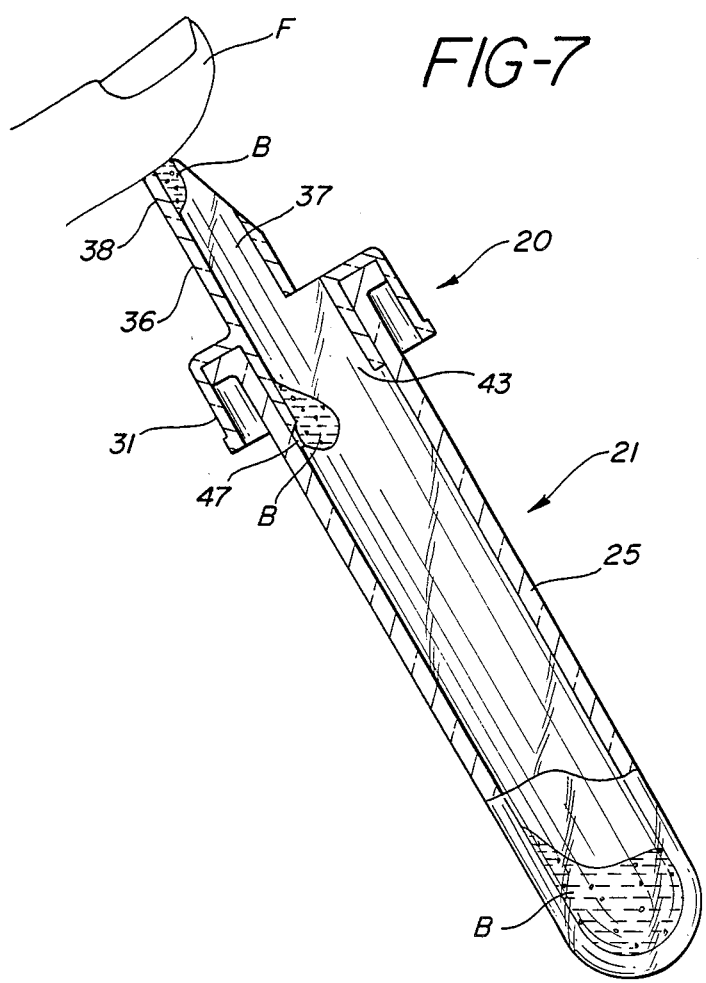

PLATELET STABLE BLOOD COLLECTION ASSEMBLY

BACKGROUND OF THE INVENTION

1. Field of the Invention

This invention relates to a blood collection assembly including a microcollection container and a collector, and more particularly relates to an assembly pretreated to improve blood flow, platelet stability and clotting resistance.

2. Background of the Invention.

Recent advancements in analytical instrumentation have made it possible to carry out a variety of hematological or chemical diagnostic procedures on very small quantities of blood, such as may be obtained by puncture of a patient's finger, earlobe or an infant's heel. Accordingly, a variety of blood sample microcollection devices have been disclosed in the art.

In designing blood microcollection equipment, several important factors have long been recognized. First, microcollection procedures typically employ skin puncture to the finger of an adult or heel of an infant. The clotting process is naturally triggered in a wound such as this and the blood entering the tube is already clotting. The clotting chain reaction must be stopped urgently to prevent its completion. Second, it is well known in the art that blood flows poorly in small diameter plastic tubes, tends to hangup on the walls of the tube and is very difficult to mix with an anticoagulant added to the tube to delay clotting. Third, the plastic surface of the tube itself is generally poorly blood compatible and may initiate clotting. These factors contribute to decreased flow into the reservoir at the bottom of the tube.

To aid in blood flow, it has been conventional in the art to add a surfactant to the tube, for example as a coating or molding additive. In addition, anticoagulants have been used to discourage clotting. Surfactants, however, may interact with the collected blood specimen and interfere with the intended analytical procedure. For example, it is known that specimens taken for platelet counting, which must be continuously mixed to maintain homogeneity during counting, often suffer platelet loss during mixing on a mechanical tube mixer.

As a result, much effort has been expended to develop blood collection devices of improved flow characteristics which allow collection and mixing of samples without the use of chemical aids such as surfactants. In early work, a cap having an integral capillary tube for engaging the puncture and conducting the blood to the container was fitted to the top of the container. However, with such an arrangement, the tip of the capillary tube had to be arranged precisely adjacent the puncture wound and the entire apparatus had to be so positioned that the blood flow along the bottom surface of the tubular microcollection container was continuous in order to engage the surface of the container. Otherwise, if a precise positioning was not carried out, blood did not readily flow from capillary tube to the reservoir where the anticoagulant was contained. Representative such collectors are taught by Blecher et al. in U.S. Pat. No. 4,024,857.

An assembly disclosed in U.S. Pat. No. 4,397,318 to Burns includes a scoop collector which is connected to the microcollection container. The scoop provides a substantially larger surface for engaging the puncture and a substantially larger transfer surface for rapidly transferring the blood from the collector into the microcollection container. Because of the relatively large surface for engaging the puncture wound, the arrangement does not require a precise positioning of the scoop in order to initiate and rapidly transfer a quantity of blood to the microcollection container.

One problem with the scoop collector taught and claimed in U.S. Pat. No. 4,397,318, although the arrangement taught therein is highly efficient for the rapid collection of a blood sample into a microcollection container, is the fact that because of the very rapid collection of blood by the scoop collector, the separate blood passage in the collector becomes somewhat occluded by the blood passing therethrough and there is hang up on the walls thereof by capillary action.

U.S. Pat. No. 4,653,512 to Losada eliminates the blood passage caused by the separate vane or wall of the scoop collector of the '318 patent. The collector of the Losada invention has longitudinal ribs extending only part way into the combined blood/air passage. The ribs contain blood flow so that the blood does not touch the walls of the combined passage through the entire circumferential extent thereof. For this reason, capillary action causing blood hang-up does not take place and blood flows rapidly through the passage. This also reduces blood sample waste in the very small total quantities involved, resulting in a larger specimen yield. Moreover, such an arrangement reduces the need for incorporating expensive blood flow agents in the collector devices of the invention.

Nugent, in U.S. Pat. No. 4,646,753 discloses a scoop collector having a plurality of discontinuities in the distal end of the body portion which facilitate more rapid transfer of blood from the collector into a container and minimize the amount of blood which must be taken from the puncture wound in order to obtain a sufficient sample in the container.

In U.S. Pat. No. 4,690,153, Losada et al. discloses a plurality of separate or integral elongated members in the form of a rod or strip or a plurality of grooves which induce a continuous blood flow from the puncture to the final blood reservoir in the container.

While the above improvements have greatly advanced the art with respect to blood flow and minimization of blood hangup and clotting, there remains a need for further improvements, particularly with respect to the platelet stability. It is toward the goal of combining the rapid blood flow of chemically treated tubes with the platelet stability of untreated tubes that the present invention is directed.

SUMMARY OF THE INVENTION

The blood collection assembly of present invention includes a plasma treated microcollection container having an open end, a closed end and a container side wall therebetween and a blood collector having a cap for engaging the open end of the container and an elongate body extending through the cap defining a longitudinal axis and having a blood flow passageway therethrough. The body also includes a scoop-shaped distal front end portion adapted to receive blood from a wound and a proximal rear end portion terminating in a proximal edge for carrying blood to an interior surface of the container side wall. Vent means is provided in the cap for air displacement therethrough. The rear end portion of the body includes a generally longitudinally extending discontinuity interrupting the edge, and the container has a plurality of members, preferably grooves, running longitudinally along a substantial length of the interior of the container side wall.

The plasma treated plastic surface has a different surface chemistry than the untreated plastic surface. Preferably, the plasma-treated surface has an oxygen to carbon ratio of about 0.05 to 0.30.

In another aspect of the invention, a method to improve blood flow and blood compatibility in a plastic blood collection assembly includes contacting plastic surfaces of the assembly with a plasma generated from a gas. Preferably, the interior wall surface of the container is contacted with a radio frequency plasma generated from oxygen.

Thus, in accordance with the invention, an improved blood collection assembly of particular value in gravity-induced sample collection using small diameter-volume plastic containers is provided. Several advantages result from the plasma alteration of the surface chemistry of the plastic container. First, the plasma-treated outside surface of the container is amenable to writing for specimen identification. Second, blood flows across the plasma treated surface and reaches the bottom of the container much more rapidly than with prior art devices. The improved blood flow substantially eliminates the tendency of the blood to hangup on the container walls. In addition, the plasma treated surface is substantially more blood compatible than the untreated surface thereby minimizing the possibility of clotting induced by contact of the blood with the container walls. Because the containers of the invention do not include any chemicals other than anticoagulant, blood samples taken therein provide platelet counts which remain substantially unchanged during storage and/or mixing between collection and testing.

BRIEF DESCRIPTION OF THE DRAWINGS

FIG. 1 is a side elevational view of one preferred blood collector of the present invention;

FIG. 2 is a bottom plan view of the preferred blood collector;

FIG. 3 is a distal end view of the preferred blood collector;

FIG. 4 is a proximal end view of the preferred blood collector;

FIG. 6b is a view in section taken along line 6b—6b of FIG. 6a; and

FIG. 7 7 is a longitudinal sectional view of the assembly of the preferred blood collector and a microcollection tube, schematically showing the collection of a blood sample from a patient.

DETAILED DESCRIPTION

Figure 5:
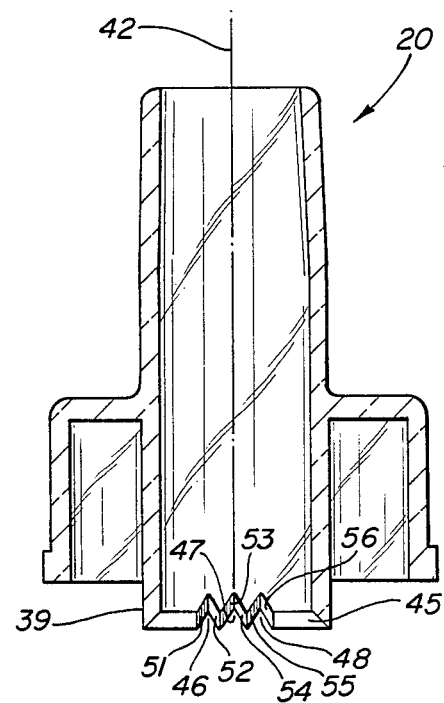
FIG. 5 is a sectional taken along line 5—5 of FIG. 1.

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments described and illustrated. The scope of the invention will be measured by the appended claims and their equivalents.

In accordance with the invention, the plastic surfaces of the blood collection assembly of the invention are treated with a plasma to alter their surface chemistry and provide improved blood flow and blood compatibility. While the invention is contemplated to include plasma treatment of all the plastic surfaces of the collector and the container, in practice it has been found that treatment of the container only provides a collection assembly of satisfactory blood flow and blood compatibility. The configuration of the container and the collector will be described first followed by a description of the plasma treatment.

Adverting to FIGS. 1-7, a blood collector 20 is for use with an elongate microcollection container or reservoir 21 having an open end 22, a closed end 23 and a cylindrically shaped side wall 25. It is within the purview of the present invention to include microcollection containers having side walls of various cross sectional shapes, and that the microcollection container described herein having a circularly shaped cross-section is exemplary of these many possibilities.

Figure 6:
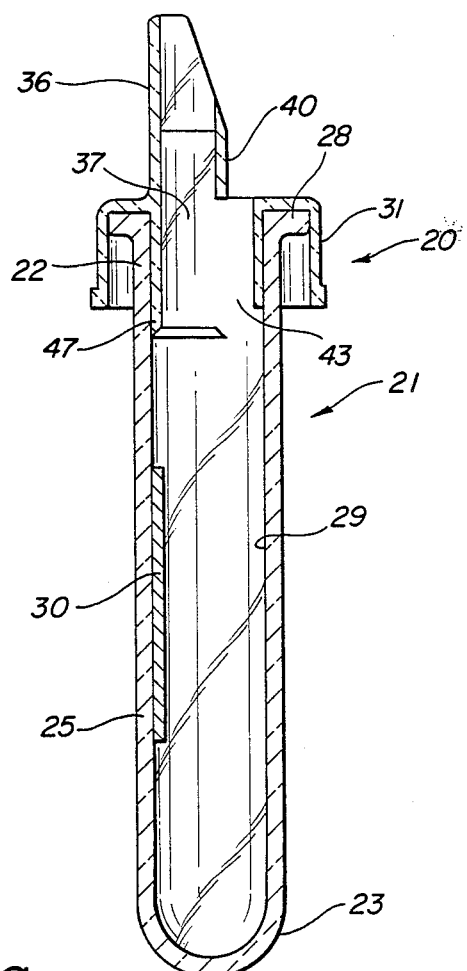
FIG. 6 is a sectional view taken along line 6—6 of FIG. 2, along with a microcollection container engaging the preferred blood collector.
Figure 6A:
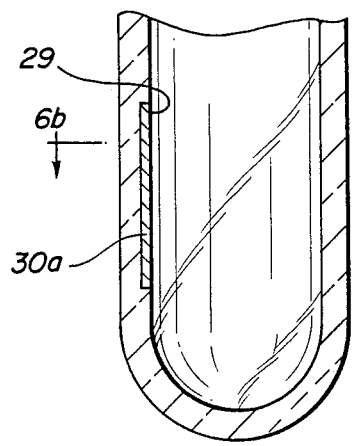
FIG. 6a is a partial sectional view in elevation of the blood collection container portion of FIG. 6 showing a groove therein.
Figure 6B:
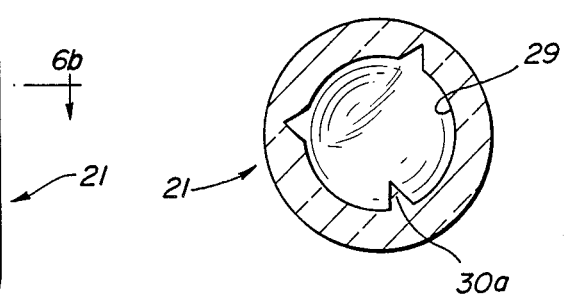

Container 21 also includes enlarged neck portion 28 and an interior surface 29 of the side wall. In preferred embodiments of container 21, one or more separate elongate members such as ribs, strips or grooves may be associated with the inside wall surface 29 of container 21. Preferably, the members are integrally molded during manufacture. FIG. 6 shows member 30 as an integral rib on surface 29. FIGS. 6a and 6b illustrate an embodiment of the invention wherein groove 30a is introduced into container 21 during molding of the plastic device.

Blood collector 20 includes a cap or cap portion 31 for removably engaging open end 22 of the microcollection container. The cap portion includes top wall 32, annular skirt 33 and interior annular skirt 34. An annular space 35 defined by the spaced skirts 33 and 34 defines a space for receiving the open end of the microcollection container in an interference or press fit arrangement. It will be apparent to one skilled in the art that numerous constructions can be used to provide a cap capable of removably engaging a microcollection container, such as structure having threads, structure providing for a snap fit, structure engaging the inside of the microcollection container in a press fit arrangement etc. and that the arrangement described herein is exemplary of these many possibilities.

A longitudinally extending, semicircular body 36, defining a longitudinal axis 42, is incorporated into the cap and extends therethrough from a scoop-shaped distal front end portion 38 to a proximal rear end portion 39 having a blood flow passageway 37 therethrough. For purposes of the description of the present invention, the term "distal end" is meant to refer to the end furthest from the person holding the microcollection container and the end closest to the source of blood, whereas the term "proximal end" is meant to refer to the end closest to the holder of the container or reservoir.

As will be explained in more detail hereinafter, body 36 is positioned with respect to cap portion 31 so that a portion of the body is adjacent to or touching interior surface 29 of side wall 25 of the container when the cap engages the container. While the blood collector of the present invention may have a body separately configured to be inserted into the cap portion wherein each of the components may be constructed separately or of different materials, it is preferred that the collector be of an integral structure.

A flat vane portion 40 of the body is spaced from front end portion 38 and extends to rear end portion 39, or, preferably, terminates at cap portion 31 to form a semi-tubular scoop. As best illustrated in FIG. 3, the body of the scoop at front end portion 38 extends for approximately 120°, shown as angle a in FIG. 3. Moving proximally from this point, the scoop body becomes larger until it merges into the vane portion at 41.

A longitudinally oriented venting conduit or vent area 43 is defined between interior annular skirt 34 and vane portion 40 of the body. The vent area provides a conduit for air to exit from the microcollection container when blood is introduced into the container through blood flow passageway 37.

Vane portion 40 and a circular portion 44 of body 36 define the blood transfer passageway 37 for rapidly transferring a quantity of blood from the surface of the patient's skin adjacent to the severed capillaries to the interior of the microcollection tube. Rear end portion 39 of body 36 preferably has a semi-circular proximal edge 45, which, in this embodiment, preferably extends for approximately 240° at which point circular portion 44 of the body joins vane portion 40 of the body. In the preferred embodiment, proximal edge 45 is tapered in a direction toward the outside bottom edge of the body so that the wall of the body becomes thinner as it approaches the proximal end.

In prior art devices, such as U.S. Pat. No. 4,397,318 to Burns alluded to above, the proximal edge is smooth and continuous throughout its length. While this configuration is contemplated to fall within the purview of the present invention, a preferred instant embodiment has a plurality of generally longitudinally 48, wherein each discontinuity extends for approximately 20° along the circumference of the body as best illustrated in FIG. 4 as angle b. It is desirable that each discontinuity should occupy no more than about 90° along the circumference of the body in a portion of the rear edge portion, with discontinuities up to about 15° to 30° being preferred.

Discontinuities 46, 47 and 48 have side walls 51 through 56 respectively. These side walls are also inclined in the same direction as proximal edge 45. In this preferred embodiment the series of substantially similarly shaped discontinuities forms a zig zag or saw tooth like shape having preferably straight side walls wherein the side walls within each discontinuity are desirably inclined at approximately 30° to 90° with respect to each other, as best illustrated in FIG. 2 as angle c, which is preferably 60° wherein each tooth is a discontinuity touching at least one adjacent discontinuity. However, it is within the purview of the present invention to include discontinuities having curved or curvilinear side walls. It is within the purview of the present invention to include blood collectors wherein the discontinuities are not substantially similarly shaped and collectors wherein the discontinuities are in a spaced relationship, separated by portions of the proximal edge. As will be explained in more detail hereinafter, it is also within the purview of the present invention to include discontinuities which project generally longitudinally outwardly from edge 45 as well as those that project generally longitudinally inwardly from edge 45 and combinations thereof.

As will be appreciated by those skilled in the art, it is most important for small quantities of blood from the severed capillaries to be transferred rapidly into the collection container. The steady flow of blood from the patient to the microcollection container is facilitated if the blood can easily travel over the transition between the proximal end of the blood flow passageway onto the interior surface of the side wall of the microcollection container. Experimental data indicates, in a comparison between collectors having the preferred saw tooth shaped discontinuities and those having a straight uninterrupted proximal edge running substantially perpendicularly to the longitudinal axis of the collector, that, when applying 25 microliter drops of blood to the test collectors which are inclined downwardly at a 45 degree angle from the horizontal it takes, on average, about six drops of blood in the blood flow conduit to initiate flow from the collector, having an uninterrupted proximal edge, into the microcollection container. By contrast, only about two drops are required, on average, to initiate flow using a collector substantially similar to the preferred embodiment described herein.

In use, a known lancet is used to puncture the patient's skin, for example at finger F, in FIG. 7, to sever blood capillaries so that the blood will escape to the surface of the skin. At this time, the blood collector of the present invention, attached to microcollection container 21, is positioned near the cut produced by the lancet and inclined downwardly so that the blood will enter scoop shaped distal front end portion 38, travel through blood flow passageway 37 to rear end portion 39 wherein the blood B passes over the semi-circular proximal edge and one or more of the discontinuities, and into the microcollection container. When a full sample is taken, the collector may be removed from the microcollection container by using a twisting and/or pulling motion to overcome the interference fit between the collector and the container, and then the sample may be covered with a separate cover, not shown, and transported to the appropriate test area. The enlarged neck portion 28 of the collector acts as a flange allowing the collector to be centrifuged to separate the serum or plasma for analysis.

Turning now to a description of the plasma treatment, both the collector and the container may be of any suitable material, rigid or flexible, such as glass or a plastic such as polyethylene, polypropylene, polyvinyl chloride, polystyrene, polyethylene terephthalate, polyacrylonitrile and polytetrafluoroethylene. The preferred material is clear or translucent polypropylene.

The container (and the collector if desired) may be placed open end up between the electrodes of a conventional plasma generator equipped with a pressure gauge, a gas inbleed and a vacuum connection. Suitable electrodes may be of any conducting material, although stainless steel and aluminum are preferred. In the most preferred configuration, parallel plate electrodes are supported horizontally in the housing of the plasma generator and the containers to be plasma treated are placed vertically therebetween. The width and shape of the electrodes is not critical. Suitable electrodes, for example, may be rectangular or circular, and may be, for example, about 20 to 60, preferably about 50 cm across.

It is preferred that the spacing of the electrodes be about 30 mm greater than the length of the container so that the plasma which diffuses into the container be as intense as possible. The bottom electrode preferably touches or nearly touches the lower electrode. While any length container may be treated, the average blood microcollection container of the invention is 43.18 mm long and 6.17 mm internal diameter, and accordingly it is preferred that the electrode be from about 65 to 95 mm apart, preferably about 80 mm apart. A plurality of containers may be supported between the electrodes in any kind of a support rack such as an acrylic plate having holes therein. Alternatively, the container may be passed through the plasma zone in a conveyer type of arrangement to facilitate automation of the plasma treatment.

For plasma treatment, the plasma generator having containers of the invention positioned between the electrodes is evacuated by attaching the vacuum connection to a suitable pump. While the final pumpdown pressure is not critical, it is preferred to reach a pumpdown pressure of about 100 mTorr. The time required to reach the pumpdown pressure of course depends on the pumping speed of the pump.

When the desired pumpdown pressure has been reached, the plasma gas is bled into the generator through the gas inbleed. Suitable gases are air, sulfur dioxide, carbon dioxide and, preferably oxygen. The gas pressure may be maintained about 10 to 1,000, preferably 50 to 400, most preferably 150 to 250 mTorr. Suitable parameters for plasma generation may be power levels of about 10 to 1,000, preferably 40 to 300, most preferably about 150 to 200 watts, RF frequency of about 1 to 100, preferably 5 to 20, most preferably the commercially available assigned 13.56 MHz, exposure times of about 5 seconds to 1 hour, preferably about 1 to 5 minutes, most preferably about 2 minutes. Less preferred plasmas may also be generated by a DC glow discharge, an audio frequency field or a microwave source.

The RF electromagnetic field generated when voltage of the desired frequency is applied to the electrodes from an RF generator ionizes the gas. The resulting plasma diffuses into the container and modifies the chemical composition of the container surface. In accordance with the invention, a significant increase in the oxygen content of the container surface is achieved by the plasma treatment, as evidenced by chemical analysis of the surface before and after plasma treatment by electron spectroscopy for chemical analysis (ESCA). A representative plasma treatment and ESCA data generated thereby is given in the Example, which is merely descriptive of the invention and not in any way intended to be limitative thereof.

EXAMPLE

Polypropylene microcollection tubes were inserted into 120 holes drilled in an acrylic plate in a 10×12 matrix. The tubes were positioned vertically with their open ends pointing upward. The plate and tubes were positioned between two 8 inch diameter aluminum electrodes 9 cm apart so that the bottom of the tubes were almost touching the lower electrode and the upper electrode was separated from the tops of the tubes by a few centimeters. The electrodes and tubes were placed inside a 12 inch diameter 22 inch tall vacuum chamber equipped for RF power delivery by a variable frequency oscillator/amplifier pair into a "T" matching network, through a balun transformer into the vacuum chamber using a sealed feedthrough, and then the balanced lines were connected to the opposing horizontal electrodes.

The chamber was pumped down to 60 mTorr over a period of 6 minutes. While continuing to pump, anhydrous oxygen was bled through a fine metering valve into the chamber at a rate sufficient to maintain a 80 mTorr pressure. After thus purging the system for 1 minute, a 10.5 MHz 35 watt RF plasma was produced for 2 minutes to treat the tubes. Following treatment, the system was vented to atmosphere and the samples removed.

The surface chemistry of the tubes was measured using ESCA and the resulting elemental compositions for treated and untreated tubes are given in Table 1.

TABLE I

| Substrate | Surface Composition % | |
|---|---|---|
| | carbon | oxygen |
| polypropylene control | 99 | 0.8 |
| polypropylene plasma-treated | 90 | 9.7 |

Platelet counts of blood specimens taken after 4 hours of mixing in the plasma treated containers of the invention were more stable that the counts obtained in untreated containers and were significantly higher than the counts obtained from the same blood specimens taken in polypropylene containers having a surfactant coating to aid flow after mixing for four hours.

Thus, it can be seen that the present invention provides a simple straight forward, reliable, easily fabricated blood collector and plasma treated microcollection container. The instant invention provides improvements over prior art blood collection assemblies in that it provides for more rapid transfer of the blood sample from the collector to the reservoir in the container, minimizes clotting, minimizes the quantity of blood which must be delivered by the puncture in order to transfer sufficient sample to the reservoir, and by avoiding chemical flow aids, eliminates the problem of platelet loss.

What is claimed is:

1. A blood collection assembly comprising:
   (a) a generally cylindrical plasma treated plastic blood collection container having an open end, a bottom wall and a side wall which together define an elongated collection chamber, said side wall having a longitudinal member associated therewith;
   (b) a plastic blood collector having a cap for removably engaging said side wall and a body portion extending through said cap for establishing blood flow between a puncture wound and said chamber; and
   (c) vent means through said cap for displacement of air from said chamber.

2. The assembly of claim wherein said plastic is selected from the group consisting of polyethylene, polypropylene, polystyrene, polytetrafluoroethylene polyethylene terephthalate, polyacrylonitrile and polyvinyl chloride.

3. The assembly of claim 1 wherein said member is an integrally molded rib.

4. The assembly of claim 1 wherein said member is an integrally molded strip.

5. The assembly of claim 1 wherein said member is a groove in said side wall.

6. The assembly of claim 1 including a plurality of members.

7. The assembly of claim 1, wherein said cap forms an interference fit with said side wall.

8. The assembly of claim 1 wherein said cap and body portion are integral.

9. The assembly of claim 1 wherein said collector is a plasma-treated collector.

10. A blood collection assembly comprising:
(a) a plasma treated blood collection container having an open end, a side wall and a bottom wall which together define a blood collection chamber;
(b) a plastic blood collector having affixing means which removably engages said side wall and a body portion extending through said affixing means for establishing blood flow between a puncture wound and said chamber; and
(c) vent means through said affixing means for displacement of air from said chamber.

11. A blood collection assembly comprising:
(a) a generally cylindrical plasma treated plastic blood collection container having an open end, a bottom wall and a side wall terminating in a lip defining said open end, said side wall having a longitudinal rib thereon, said side and bottom walls together defining an elongated blood collection chamber;
(b) a plastic blood collector having a cap for removably engaging said lip and a body portion extending through said cap and defining a passageway for blood flow between a puncture wound and said chamber, the proximal edge of said body portion including a generally longitudinally extending discontinuity interrupting said edge;
(c) a vent through said plastic cap for displacement of air from said container; and
(d) a vane portion of said body portion separating said vent from said passageway.

12. The blood collector of claim 11 wherein said discontinuity extends inwardly from said proximal edge.

13. The blood collector of claim 12 wherein said discontinuity has substantially straight side walls.

14. The blood collector of claim 11 wherein said discontinuity extends outwardly from said proximal edge.

15. The blood collector of claim 14 wherein said discontinuity has substantially straight side walls.

* * * * *

Disclaimer and Dedication

4,967,763—*Edward Nugent*, North Caldwell, N.J.; *Robert J. Losada*, Astoria, N.Y.; *Hugh T. Conway*, Verona, N.J.; *David B. Montgomery; Joel L. Williams*, both of Cary, N.C. PLATELET STABLE BLOOD COLLECTION ASSEMBLY. Patent dated Nov. 6, 1990. Disclaimer and Dedication filed June 6, 1991, by the assignee, Dickinson and Co.

Hereby disclaims and dedicates to the Public all claims of said patent.
[ *Official Gazette August 27, 1991* ]